(12) United States Patent
Roberts et al.

(10) Patent No.: US 12,195,710 B2
(45) Date of Patent: Jan. 14, 2025

(54) INCUBATOR (71) Applicant: Cook Medical Technologies LLC, Bloomington, IN (US)

(72) Inventors: Erin E. Roberts, Bloomington, IN (US); Jorge L. Jimenez-Rios, Bloomington, IN (US); Jaimie M. Jarboe, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 544 days.

(21) Appl. No.: 17/165,558

(22) Filed: Feb. 2, 2021

(65) Prior Publication Data
US 2021/0246406 A1    Aug. 12, 2021

Related U.S. Application Data (60) Provisional application No. 62/971,683, filed on Feb. 7, 2020.

(51) Int. Cl.
C12M 1/00    (2006.01)
C12M 1/12    (2006.01)
(Continued)

(52) U.S. Cl.
CPC ............ *C12M 23/48* (2013.01); *C12M 25/06* (2013.01); *C12M 33/00* (2013.01); *C12M 41/14* (2013.01)

(58) Field of Classification Search
CPC ...... C12M 21/06; C12M 23/10; C12M 23/48; C12M 23/50; C12M 25/06; C12M 33/00; C12M 41/14; C12M 41/36
See application file for complete search history.

(56) References Cited

U.S. PATENT DOCUMENTS 6,623,956 B1    9/2003    Cecchi et al.
6,673,595 B2    1/2004    Barbera-Guillem
(Continued)

FOREIGN PATENT DOCUMENTS

AU    2001249559 B2    7/2002
EP    2 586 858 A1    5/2013
(Continued)

OTHER PUBLICATIONS

Extended European Search Report from corresponding European application No. 21155293.9-1132, Jul. 2, 2021, 7 pp.
(Continued)

*Primary Examiner* — Lydia Edwards
(74) *Attorney, Agent, or Firm* — Crowell & Moring LLP (57) ABSTRACT A device for culturing specimens may include a housing and a conveyor disposed within the housing, where the conveyor is translatable in vertical directions. The device may further include a plurality of plate holders disposed along a length of the conveyor, such that each plate holder of the plurality of plate holders can be moved to different positions along the length of the conveyor by a translation of the conveyor in the vertical directions. The device may further include an isolation chamber movable between a first position and a second position. The isolation chamber may include an opening and a door. The isolation chamber may be configured such that when the isolation chamber is in the second position, a first plate holder of the plurality of plate holders is isolated from a rest of the housing by the isolation chamber.

17 Claims, 4 Drawing Sheets (51) Int. Cl.
*C12M 1/26* (2006.01)
*C12M 3/00* (2006.01)

(56) References Cited

U.S. PATENT DOCUMENTS

| | | | |
|---|---|---|---|
| 7,816,126 | B2 | 10/2010 | Kagayama et al. |
| 9,404,074 | B2 | 8/2016 | Kiyota |
| 2004/0152188 | A1 | 8/2004 | Yamamoto et al. |
| 2005/0069401 | A1 | 3/2005 | Malin |
| 2008/0213873 | A1 | 9/2008 | Murray et al. |
| 2008/0318307 | A1 | 12/2008 | Spittle et al. |
| 2009/0029450 | A1 | 1/2009 | Nakamura et al. |
| 2009/0068728 | A1 | 3/2009 | Kiyota et al. |
| 2009/0185956 | A1 | 7/2009 | Junger et al. |
| 2010/0126286 | A1* | 5/2010 | Self .................. G01N 35/04 73/863.81 |
| 2014/0030802 | A1 | 1/2014 | Eberle et al. |
| 2016/0325284 | A1* | 11/2016 | Camillo ............. B01L 3/50851 |
| 2017/0009195 | A1 | 1/2017 | Ramsing et al. |
| 2017/0009202 | A1 | 1/2017 | Ramsing et al. |
| 2017/0146460 | A1 | 5/2017 | Cecchi et al. |
| 2018/0079999 | A1 | 3/2018 | Blanchard |
| 2018/0112164 | A1 | 4/2018 | Cecchi et al. |
| 2018/0346868 | A1 | 12/2018 | Blanchard |
| 2018/0371396 | A1 | 12/2018 | Makino et al. |

FOREIGN PATENT DOCUMENTS

| | | |
|---|---|---|
| WO | WO 2004027016 A1 | 4/2004 |
| WO | WO 2018204007 A1 | 11/2018 |

OTHER PUBLICATIONS http://vf-concern.am/image/data/PDF/K-Systems.%20samlet_web_16-17.pdf, K-Systems 2016 & 17 Catalogue, Webpage accessed Jul. 23, 2019, 48 pgs.

http://escolifesciences.us/products/download/art-equipment-miri-tl-brochure-vc-ir.pdf, Miri TL Time Lapse Incubator for IVF, Webpage first available Mar. 19, 2015, 8 pgs.

EP Examination Report regarding Application No. 21 155 298.9 dated Jun. 26, 2023, 5 pages.

* cited by examiner

INCUBATOR

CROSS-REFERENCE TO RELATED APPLICATIONS

This patent application claims priority from U.S. Provisional Application No. 62/971,683, filed Feb. 7, 2020, the entirety of which is hereby fully incorporated by reference herein.

TECHNICAL FIELD

The present disclosure relates to a vertical storage incubator intended to increase storage capacity, reduce footprint of an incubator, and/or more closely mimic an in vivo environment.

BACKGROUND

In cell culturing applications, such as in vitro fertilization (IVF) cell culture, incubators are intended to allow for hands off incubation of specimens (e.g., embryos) from post-fertilization until they are prepared for transfer or vitrification. Conditions within the incubator, such as atmospheric composition, pH, temperature, and incubation time are controlled to mimic the in vivo environment in which embryotic development occurs.

BRIEF SUMMARY OF THE INVENTION

One general aspect of the present disclosure includes a device for culturing specimens, including: a housing; a conveyor disposed within the housing, the conveyor being translatable in vertical directions; a plurality of plate holders disposed along a length of the conveyor, such that each plate holder of the plurality of plate holders can be moved to different positions along the length of the conveyor by a translation of the conveyor in the vertical directions; and an isolation chamber movable between a first position and a second position, the isolation chamber including an opening and a door, where the isolation chamber is configured such that when the isolation chamber is in the second position, a first plate holder of the plurality of plate holders is isolated from a rest of the housing by the isolation chamber.

Another general aspect of the present disclosure includes a device for culturing specimens, including: a housing; a conveyor disposed within the housing, the conveyor being translatable in vertical directions; a plurality of plate holders disposed along a length of the conveyor, such that each plate holder of the plurality of plate holders can be moved to a first position and a second position along the length of the conveyor by a translation of the conveyor in the vertical directions; and an isolation chamber movable between a third position and a fourth position, the isolation chamber including an opening and a door, where the isolation chamber is configured such that when the isolation chamber is in the fourth position, a first plate holder of the plurality of plate holders located in the first position is isolated from a rest of the housing by the isolation chamber.

Another general aspect of the present disclosure includes a device for culturing specimens, including: a housing; a conveyor disposed within the housing, the conveyor being translatable in vertical directions; and a plurality of plate holders disposed along a length of the conveyor, such that each plate holder of the plurality of plate holders can be moved to different positions along the length of the conveyor by a translation of the conveyor in the vertical directions, where each plate holder of the plurality of plate holders is configured for supporting a plate thereon such that the plate can be moved to the different positions along the length of the conveyor by the translation of the conveyor in the vertical directions while maintaining a horizontal orientation of the plate.

Other systems, methods, features and advantages of the presently disclosed embodiments will be, or will become, apparent to one with skill in the art upon examination of the following figures and detailed description. It is intended that all such additional systems, methods, features, and advantages be within the scope of the invention.

BRIEF DESCRIPTION OF THE DRAWINGS

The present disclosure can be better understood with reference to the following drawings and description. The components in the figures are not necessarily to scale, emphasis instead being placed upon illustrating the principles of the present disclosure. Moreover, in the figures, like-referenced numerals designate corresponding parts throughout the different views.

DETAILED DESCRIPTION

Various aspects are described below with reference to the drawings in which like elements generally are identified by like numerals. The relationship and functioning of the various elements of the aspects may better be understood by reference to the following detailed description. However, aspects are not limited to those illustrated in the drawings or explicitly described below. It also should be understood that the drawings are not necessarily to scale, and in certain instances details may have been omitted that are not necessary for an understanding of aspects disclosed herein, such as conventional material, construction, and assembly.

Figure 1:
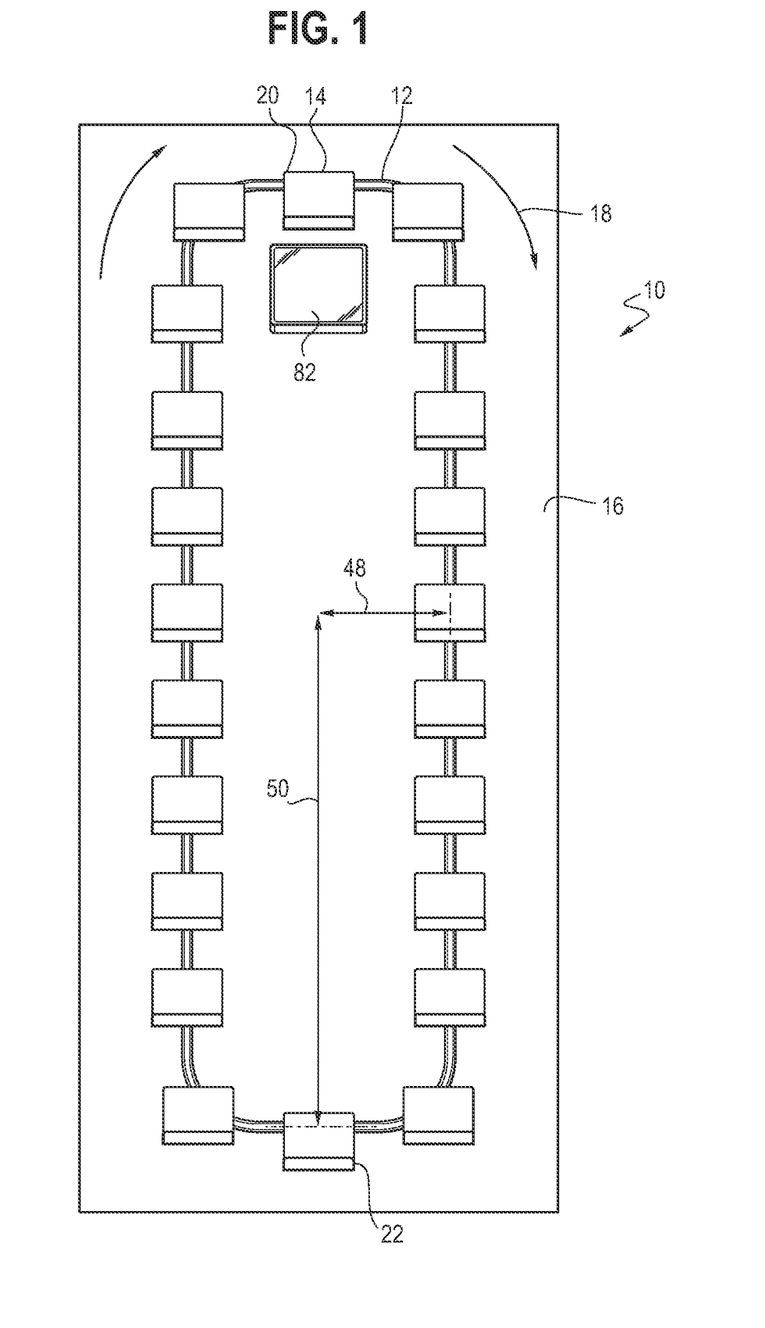
FIG. 1 is a schematic front view of a device including a conveyor and a plurality of plate holders disposed thereon in accordance with certain aspects of the present disclosure.

Turning now to FIGS. 1-6, a device 10 for culturing specimens is provided. While, in some embodiments, an incubator device for use in IVF is specifically described, it will be appreciated that the device 10 may be successfully implemented for use in other cell culture processes to achieve a greater storage capacity and a better controlled environment for culturing the cells. In an exemplary embodiment, constructed as an incubator for one or more embryos, conditions within the incubator, such as atmospheric composition, pH, and temperature, are controlled to mimic the in vivo environment in which embryotic development occurs. One of ordinary skill in the art, with a thorough review of the subject specification and figures, would readily comprehend how the device 10 may be implemented for use in other types of cell culture processes and would readily comprehend which cells and which other types of cell culture processes might be suitable without undue experimentation. The device 10 includes a housing 16 and a conveyor 12 disposed within the housing 16. In some embodiments, as shown in FIG. 1, the conveyor 12 has a loop configuration and is configured to hold a plurality of plate holders 14 spacingly along a length of the conveyor 12 (i.e., a plurality of plate holders 14 are disposed along a length of the conveyor 12). The shape and size of the loop may be varied (e.g., generally oval as shown in FIG. 1; generally circular), as desired and/or needed, to achieve a desired storage capacity of the device 10, as discussed in greater detail below. The conveyor 12 may include a plurality of receiving sections (e.g., apertures) disposed spacingly along the length of the conveyor 12 (e.g., along the circumference of the loop). The receiving sections are configured to receive and support the plate holders 14, as discussed in greater detail below.

Figure 6:
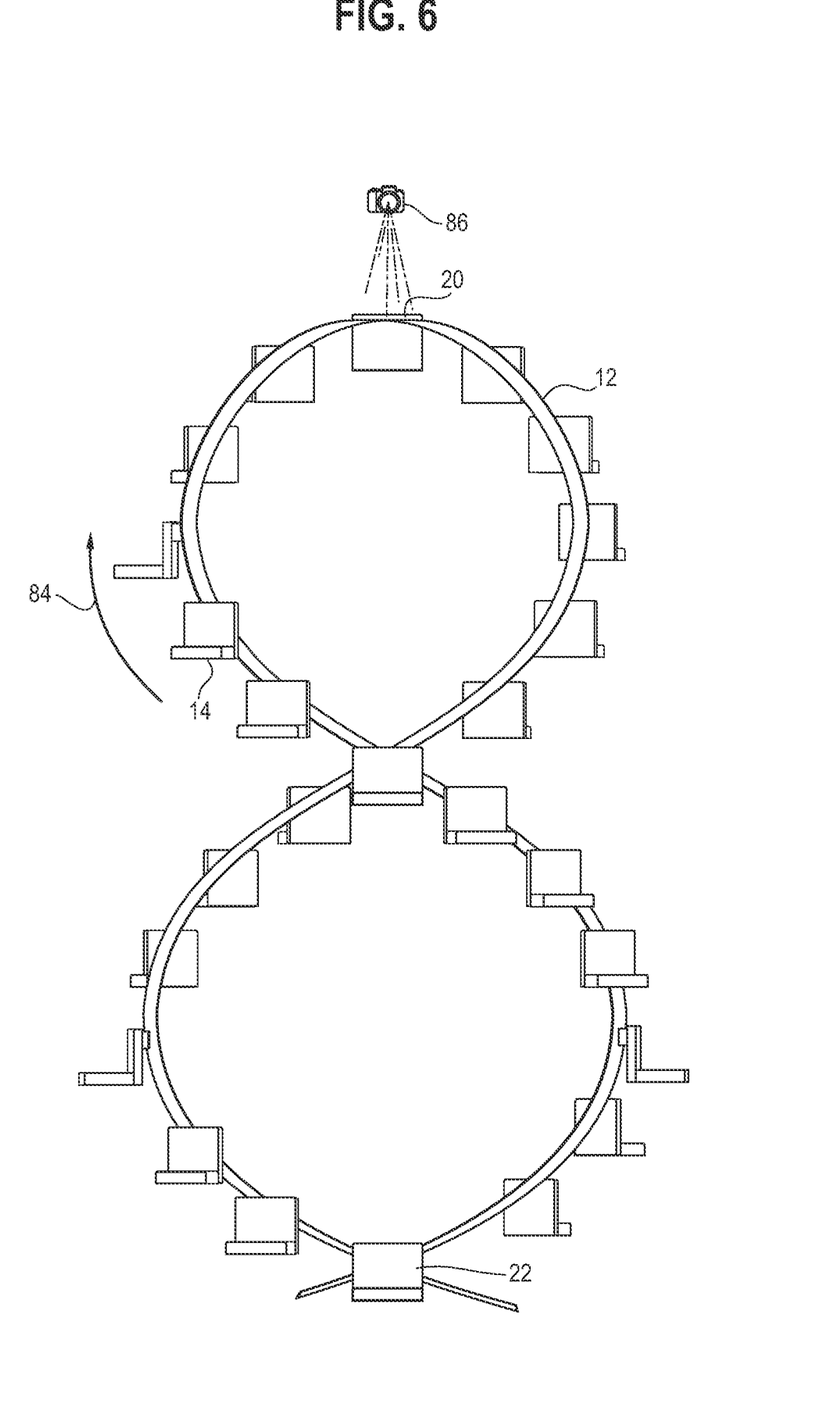
FIG. 6 is a schematic front view of another embodiment of the conveyor and a plurality of plate holders disposed thereon in accordance with certain aspects of the present disclosure.

The conveyor 12 is configured to be translatable along a line (e.g., the line of the shape/periphery of the conveyor 12) that provides for the plate holders 14 to complete a circuit of the conveyor 12 without dislodging plates from the plate holders 14. In some embodiments, the conveyor 12 is translatable in vertical directions and/or in both horizontal and vertical directions. The terms "horizontal" and "horizontally" are intended to describe the directions with respect to the plane the device 10 is disposed upon (e.g., a top surface of a table) and are intended to include the specific directions referenced as well as a direction that is within 5 degrees around the direction referenced. The terms "vertical" and "vertically" are intended to describe the directions with respect to the plane the device 10 is disposed upon (e.g., a top surface of a table) and are intended to include the specific directions referenced as well as a direction that is within 75 degrees around the direction referenced, while some embodiments may be exactly vertical, within 60 degrees or within 45 degrees of exactly vertical, or anywhere in between. In some embodiments, as shown in FIG. 1, the conveyor 12 is translatable in the direction 18 (clockwise) in a vertical plane, which allows each of the plate holders 14 to be moved to different positions along the length of the conveyor 12 (e.g., along the circumference of the loop), including the uppermost position 20 and the lower most position 22. In some embodiments, the conveyor 12 may be translatable in other directions (e.g., counterclockwise) to move the plate holders 14 to different positions. For example, in some embodiments, as shown in FIG. 6, the conveyor 12 has a helical or spiral configuration and is translatable in vertical directions (e.g., as shown by the arrow 84), such that each plate holder 14 disposed on the conveyor 12 can be moved to different positions (including the uppermost position 20 and the lower most position 22) along the length of the conveyor 12 by the translation of the conveyor 12 in the vertical directions. While some features may be specifically described and depicted with reference to the embodiment of the conveyor 12 shown in FIG. 1, a person of ordinary skill in the art with a thorough review of the specification and the figures will readily comprehend how these features may be included in the embodiment of the conveyor 12 shown in FIG. 6.

Figure 4:
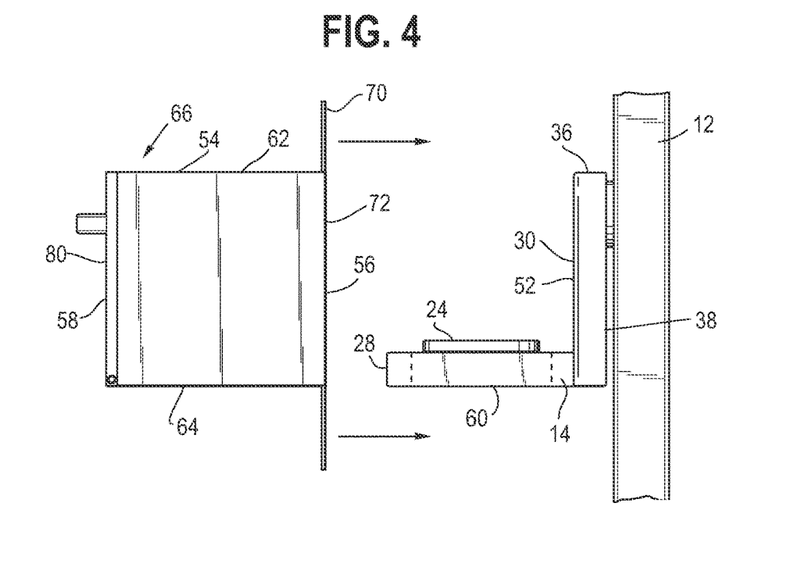
FIG. 4 is a schematic side view showing an isolation chamber moving towards a plate holder of FIG. 1 in accordance with certain aspects of the present disclosure.

Each of the plate holders 14 is configured for supporting a plate 24 (e.g., as shown in FIG. 4) thereon, where the plate 24 is configured to receivingly support specimens (e.g., embryos). Disposing the plate holders 14 spacingly along the length of the conveyor 12 (e.g., along the circumference of the loop) that is translatable in the vertical directions (e.g., in the vertical plane) is advantageous for allowing the plates 24 of specimens to be stored vertically, which would increase the storage capacity of the device 10 without the need for increasing the footprint of the device 10. The vertical storage capacity of the device 10 would allow labs to handle more specimens at one time with the same number of operators (e.g., embryologists). It will be appreciated that by varying the shape and/or size of the loop configuration of the conveyor 12, a desired storage capacity and footprint may be achieved. For example, a loop configuration with a minor axis 48 disposed horizontally and a major axis 50 disposed vertically, as shown in FIG. 1, will provide a relatively high storage capacity and relatively small footprint. While in some embodiments, as shown in FIG. 1, only one conveyor 12 is included in the device 10, it will be appreciated that two or more conveyors 12 may be included in the device 10 to further increase the storage capacity, as desired and/or needed, without departing from the scope of the present invention.

Figure 3A:
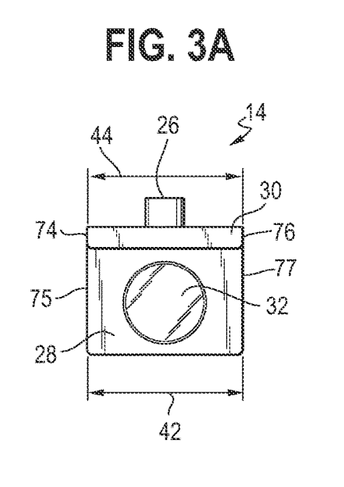
FIG. 3A is a schematic top view of a plate holder of FIG. 1 in accordance with certain aspects of the present disclosure.
Figure 3B:
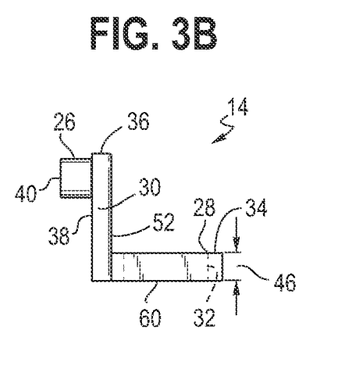
FIG. 3B is a schematic side view of the plate holder of FIG. 3A in accordance with certain aspects of the present disclosure.
Figure 3C:
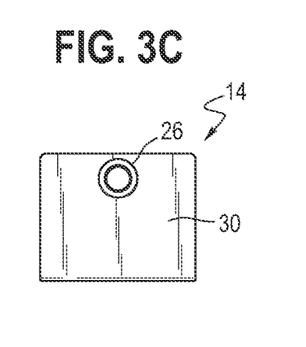
FIG. 3C is a schematic back view of the plate holder of FIG. 3A in accordance with certain aspects of the present disclosure.

In some embodiments, as shown in FIGS. 3A-3C, each plate holder 14 includes an upper portion 26 configured to couple to the conveyor 12, a lower portion 28 configured to support a plate 24 thereon, and a middle portion 30 disposed between the upper portion 26 and the lower portion 28. A back surface 38 of the middle portion 30 contacts the upper portion 26 and a front surface 52 of the middle portion 30 contacts the lower portion 28. The upper portion 26, the lower portion 28, and the middle portion 30 are integrally formed or coupled together. As shown in FIGS. 3A-3C, the middle portion 30 extends outwardly (e.g., substantially perpendicular) from a top surface 34 of the lower portion 28 to a top surface 36 of the middle portion 30. The term "substantially perpendicular" is specifically defined herein to include 90 degrees as well as a continuous range of angles between 85 degrees and 95 degrees. In some embodiments, as shown in FIG. 3A, the middle portion 30 may have a width 44 that is generally the same as the width 42 of the lower portion 28. In some embodiments, as shown in FIGS. 3A-3B, the lower portion 28 may include a transparent section 32 extending through the thickness 46 of the lower portion 28 and configured for light transmission for imaging, as discussed in greater detail below.

In some embodiments, as shown in FIGS. 3A-3C, the upper portion 26 extends outwardly (e.g., substantially perpendicular) from the back surface 38 of the middle portion 30 to a distal end 40 of the upper portion 26. The cross-section of the upper portion 26 may have any configuration (e.g., generally circular as shown in FIG. 3C), depending on the configuration of the corresponding receiving section of the conveyor 12, without departing from the scope of the present invention, as long as the plate holder 14 can be coupled to the conveyor 12 at a desired location (e.g., by coupling the upper portion 26 to the corresponding receiving section of the conveyor 12).

The configuration of the plate holders 14, discussed above, allows the plate holders 14 to be coupled to the conveyor 12 at desired locations such that the plates 24 can be disposed on the plate holders 14 and can be moved to different positions along the length of the conveyor 12 by the translation of the conveyor 12 in the vertical directions while maintaining the horizontal orientation of the plates 24. For example, as shown in FIG. 1, when the plate holders 14 are coupled to the conveyor 12 (e.g., the upper portion 26 of the plate holder 14 is coupled to the conveyor 12), the lower portion 28 extends horizontally such that plates 24 can be placed on and supported by the top surface 34 of the lower portion 28. During the translation of the conveyor 12 in the vertical plane, the plate holders 14 can be moved to different locations, with the front surfaces 52 of the middle portions 30 of the plate holders 14 always facing the same direction (e.g., facing the front wall 70 (e.g., as shown in FIG. 4) of the housing 16), with the lower portions 28 of the plate holders 14 maintaining horizontal, and with the plates 24 maintaining a horizontal orientation on the lower portions 28 of the plate holders 14. This configuration is advantageous for allowing certain positions along the length of the conveyor 12 to be associated with specific operations (e.g., imaging, inserting plates into the housing, and/or removing plates from the housing), such that all the plate holders 14 (and thus the plates 24 disposed thereon) can be moved to these positions with the plates 24 maintaining a horizontal orientation, thereby allowing specific operations to be performed on any desired plate 24 (and thus the specimens disposed thereon) through the translation of the conveyor 12, as discussed in greater detail below.

Figure 5:
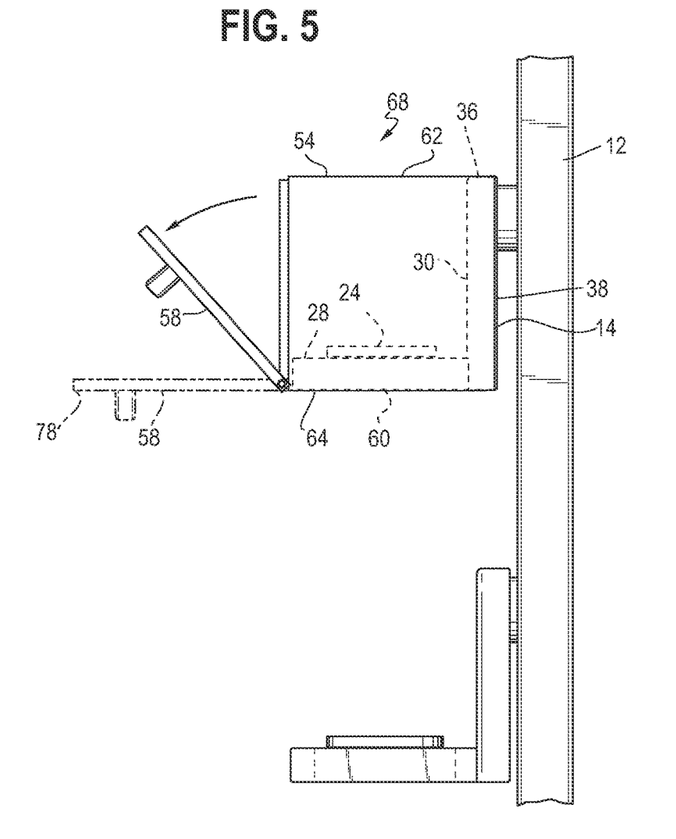
FIG. 5 is a schematic side view showing a plate holder of FIG. 1 received within the isolation chamber of FIG. 4 in accordance with certain aspects of the present disclosure.

In some embodiments, as shown in FIGS. 4-5, the device 10 may include an isolation chamber 54. The isolation chamber 54 may be disposed at a desired location on the front wall 70 of the housing 16 such that each of the plate holders 14 can be moved into registry with the isolation chamber 54 by the translation of the conveyor 12 in the vertical directions (e.g., in the vertical plane). The isolation chamber 54 is movable between a first position 66 (e.g., outside the housing 16, as shown in FIG. 4) and a second position 68 (e.g., inside the housing 16, as shown in FIG. 5). When the isolation chamber 54 is in the second position 68, the conveyor 12 is prevented from moving.

The isolation chamber 54 may include an opening 56 and a door 58 disposed on opposite sides of the isolation chamber 54. When the isolation chamber 54 is in the first position 66, the section 72 of the front wall 70 that is in registry with the opening 56 may be closed, such that the housing 16 is in a closed configuration, where no plates 24 can be inserted into or removed from the housing 16. To move the isolation chamber 54 to the second position 68, the section 72 of the front wall 70 that is in registry with the opening 56 will be opened (e.g., moved out of the way), such that the isolation chamber 54 can be moved into the housing 16.

In some embodiments, the isolation chamber 54 is configured such that as the isolation chamber 54 is moved into the housing 16 and to the second position 68, a plate holder 14 (e.g., first plate holder) that is disposed in registry with the opening 56 of the isolation chamber 54 will be received within the isolation chamber 54 through the opening 56. In some embodiments, the isolation chamber 54 is also configured such that when the isolation chamber 54 is in the second position 68, the plate holder 14 that is received within the isolation chamber 54 is isolated from the rest of the housing 16 by the isolation chamber 54. For example, as shown in FIGS. 3A and 5, the isolation chamber 54 is configured such that when the plate holder 14 is received within the isolation chamber 54, the upper surface 62 of the isolation chamber 54 sealingly engages the top surface 36 of the middle portion 30 of the plate holder 14, the bottom surface 64 of the isolation chamber 54 sealingly engages the bottom surface 60 of the lower portion 28 of the plate holder 14, the side surfaces of the isolation chamber 54 sealingly engage the side surfaces 74 and 76 of the middle portion 30 of the plate holder 14, respectively, and the side surfaces of the isolation chamber 54 also sealingly engage the side surfaces 75 and 77 of the lower portion 28 of the plate holder 14, respectively. As a result, the plate holder 14 received in the isolation chamber 54 in the second position 68 is isolated from the rest of the housing 16. The respective engaging surfaces of the isolation chamber 54 and/or the plate holder 14 may be provided with a resilient material such as rubber or foam, arranged to help with the sealing.

It will be appreciated that the configuration of the isolation chamber 54 may be varied, depending on the configuration of the plate holder 14, without departing from the scope of the present invention, as long as when the plate holder 14 is received within the isolation chamber 54, respective surfaces of the plate holder 14 and the isolation chamber 54 sealingly engage each other, such that the plate holder 14 that is received within the isolation chamber 54 is isolated from the rest of the housing 16 by the isolation chamber 54.

In some embodiments, as shown in FIGS. 4 and 5, the door 58 is movable between an open position 78 and a closed position 80. As shown in FIG. 5, when the isolation chamber 54 is in the second position 68 and the door 58 is opened, the plate holder 14 received in the isolation chamber 54 through the opening 56 will be in fluid communication with an environment outside the housing 16 while the rest of the housing 16 is isolated from the environment outside the housing. Accordingly, the isolation chamber 54 is configured to allow a plate to be placed onto or removed from a plate holder of the plurality of plate holders 14 without exposing other plate holders of the plurality of plate holders 14 in the housing 16 to the environment outside the housing 16. For example, when the isolation chamber 54 is in the second position 68 and the door is in the open position 78, a plate 24 (e.g., a first plate) can be inserted into the isolation chamber 54 from the environment outside the housing 16 and be placed on the plate holder 14 received within the isolation chamber 54 (e.g., when there is no plate 24 disposed on the plate holder 14) or a plate 24 (e.g., a second plate) already placed on the plate holder 14 can be taken out of the housing 16 through the door 58 of the isolation chamber 54, without affecting the conditions in the rest of the housing 16. This is advantageous for allowing plates to be inserted into and removed from the housing 16 without exposing any of other plates 24 (and the specimens disposed thereon) in the rest of the housing 16 to the environment outside the housing 16, thereby improving the environmental/condition control inside the housing 16 (e.g., oxygen concentration, pH, and temperature) and providing better cell culture outcomes due to more closely reflecting the in vivo conditions.

In some embodiments, the device 10 may be automatically controlled to move the conveyor 12, the isolation chamber 54, the door 58 of the isolation chamber 54, and the section 72 of the front wall 70 that is in registry with the opening 56 of the isolation chamber 54. For the sake of brevity, a method of automatically controlling the movements discussed above for inserting a plate 24 into the housing 16 and removing a plate 24 from the housing 16 will be described in detail below, but it will be appreciated that at least one of the movements discussed above may be performed manually by an operator. One of ordinary skill in the art with a thorough review of the specification and the figures will readily comprehend how and which of the movements can be performed manually by an operator.

In use, to insert a plate 24 into the housing 16 or removing a plate 24 from the housing 16 without exposing other plates 24 in the housing 16 to the environment outside the housing 16, the conveyor 12 is automatically translated in the vertical directions (e.g., in the vertical plane) until a desired plate holder 14 is moved into registry with the opening 56 of the isolation chamber 54, then the conveyor 12 is automatically stopped translating such that the desired plate holder 14 is held in place and prevented from moving. Then, the section 72 of the front wall 70 of the housing 16 that is in registry with the opening 56 of the isolation chamber 54 is automatically moved out of the way such that a passageway on the front wall 70 is formed for the isolation chamber 54 to be moved into the housing 16 through the passageway. Then, the isolation chamber 54 is automatically moved to the second position 68 inside the housing 16, through the passageway, such that the desired plate holder 14 is sealingly received within the isolation chamber 54, as discussed above.

Then, the door 58 of the isolation chamber 54 is automatically opened and moved to the open position 78. Then, a plate 24 will be inserted into the isolation chamber 54 from the environment outside the housing 16 and be placed on the desired plate holder 14 (in the operation of inserting a plate) or a plate 24 already placed on the desired plate holder 14 will be taken out of the housing 16 through the door 58 of the isolation chamber 54 (in the operation of removing a plate), without affecting the conditions in the rest of the housing 16. Then, the door 58 is automatically closed (moved into the closed position 80). Then, the isolation chamber 54 is automatically moved to the first position 66 outside the housing 16. Then, if another plate 24 needs to be inserted into or removed from the housing 16, the conveyor 12 is automatically translated to move another desired plate holder 14 into registry with the opening 56 of the isolation chamber 54, and the steps discussed above will be repeated. When no other plates 24 need to be inserted into or removed from the housing 16, the section 72 of the front wall 70 of the housing 16 is automatically moved to its original place (closed), blocking the passageway on the front wall 70, such that the housing 16 is in the closed configuration, where no plates 24 can be inserted into or removed from the housing 16.

Figure 2:
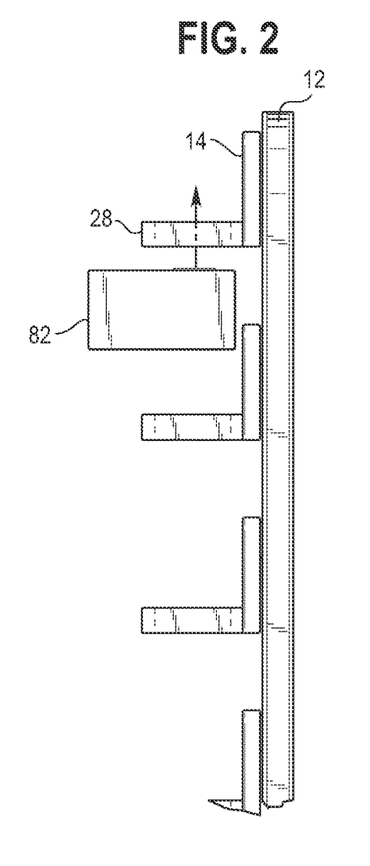
FIG. 2 is a schematic side view showing a portion of the device of FIG. 1 in accordance with certain aspects of the present disclosure.

In some embodiments, as shown in FIGS. 1, 2 and 6, an imaging position (such as, by way of non-limiting example, the uppermost position 20) is associated with an imaging system 82 for imaging the specimens disposed on the plate 24, supported by a plate holder 14, which is moved to the imaging position. The imaging system 82 may include a light source positioned in the housing 16 and underneath the plate holder 14 in the imaging position for illuminating the specimens through the transparent section 32 of the lower portion 28 of the plate holder 14. The imaging system 82 may also include a camera 86 disposed in the housing 16 and underneath the plate holder 14 in the imaging position or disposed outside the housing 16 above the imaging position (e.g., shown in FIG. 6 as uppermost position 20), and the camera 86 is configured for capturing images of the specimens disposed on the plate 24 that is in the imaging position. In some embodiments, a microscope may be placed outside the housing 16 and above the imaging position and configured to monitor the conditions of the specimens disposed on the plate 24 that is in the imaging position. This configuration is advantageous for allowing any desired plate 24 to be monitored and/or imaged inside the housing 16, simply by moving it to the imaging position by the translation of the conveyor 12 in the vertical directions (e.g., in the vertical plane), without the need for taking it out of the housing 16, thereby enhancing the stability of the controlled environment in the housing 16 and achieving better cell culture outcomes due to more closely reflecting the in vivo conditions.

In some embodiments, the device 10 (e.g., used in IVF) may be configured such that the temperature within the housing 16 is controlled such that the temperature within the housing 16 is changeable based upon a schedule (e.g., changing cyclically). The schedule and the temperature change may be configured to mimic circadian rhythms of a human female, such that small temperature variations are provided in the housing 16 from day to night, as are known to occur in a human body. In some embodiments, the device 10 (e.g., used in IVF) may be configured such that the pressure within the housing 16 is controlled to mimic typical intratubal or intrauterine pressure of a human female, such as by matching the waveform of intrabdominal pressure caused by breathing. In some embodiments, the device 10 may be configured to move (e.g., cyclically) or agitate the specimens disposed within the housing 16, and the movement or agitation of the specimens is at a greater frequency or magnitude during daytime periods in a geographic location where the device 10 is operated and at a lower frequency or magnitude during nighttime periods in the geographic location where the device 10 is operated. In some embodiments, the device 10 may be configured to expose (e.g., cyclically) the specimens disposed in the housing 16 to sound waves that are representative of sound waves created by humans talking, as one example of a form of agitation, where other forms of agitation may include more or less kinetic energy.

In some embodiments, the device 10 (e.g., used in IVF) may be configured such that different regions in the housing 16 have different conditions in order to reflect different physiological conditions that would be experienced as an embryo moves from the fallopian tubes into the uterine cavity or to reflect different uterine conditions that would be experienced as an embryo incubates from day 1 to day 5 or 6. In some embodiments, the different conditions may include different temperature, pressure, humidity, and any other suitable physiological conditions of a human female. In some embodiments, the device 10 may be configured to monitor and record the quality control (QC) information of the specimens disposed within the housing 16 and communicate the QC information to external equipment that is in communication with the device 10. In some embodiments, the external equipment may include laboratory quality management systems. In some embodiments, the device 10 may be configured to communicate developmental data regarding the specimens disposed within the housing 16 as monitored by the device 10 with external laboratory management equipment. For example, the device 10 may be configured to interface with laboratory management software to record developmental data of the specimens (e.g., embryos). In some embodiments, the device 10 may be configured to accommodate (e.g., read) bar code labeling of culture plates, RFID chips, or another device of wireless communication acting as an electronic witnessing system.

While various embodiments of the present disclosure have been described, the present disclosure is not to be restricted except in light of the attached claims and their equivalents. One skilled in the relevant art will recognize that numerous variations and modifications may be made to the embodiments described above without departing from the scope of the present invention, as defined by the appended claims. Moreover, the advantages described herein are not necessarily the only advantages of the present disclosure and it is not necessarily expected that every embodiment of the present disclosure will achieve all of the advantages described.

We claim:

1. A device for culturing specimens, comprising:
a housing;
a conveyor disposed within the housing, the conveyor being translatable in vertical directions with respect to a plane the housing is disposed upon;
a plurality of plate holders disposed along a length of the conveyor, such that each plate holder of the plurality of plate holders can be moved to different positions along the length of the conveyor by a translation of the conveyor in the vertical directions; and
an isolation chamber movable between a first position and a second position,
wherein the isolation chamber includes an opening and a door disposed on a side of the isolation chamber opposite of the opening, and
wherein the isolation chamber is configured such that when the isolation chamber is moved to the second position, a first surface of the isolation chamber sealingly engages a second surface of a first plate holder of the plurality of plate holders.

2. The device for culturing specimens of claim 1, wherein the conveyor is translatable in a vertical plane with respect to the plane the housing is disposed upon or the conveyor has a helical or spiral configuration.

3. The device for culturing specimens of claim 1,
wherein the door is movable between an open position and a closed position, wherein when the isolation chamber is in the second position and the door is in the open position, the first plate holder is received within the isolation chamber through the opening and is in fluid communication with an environment outside the housing while the rest of the housing is isolated from the environment outside the housing, and/or
wherein when the isolation chamber is in the second position and the door is in the open position, a first plate can be inserted into the isolation chamber from the environment outside the housing and placed on the first plate holder or a second plate placed on the first plate holder can be taken out of the housing through the door of the isolation chamber.

4. The device for culturing specimens of claim 1, wherein each plate holder of the plurality of plate holders is configured for supporting a plate thereon such that the plate can be moved to the different positions along the length of the conveyor by the translation of the conveyor in the vertical directions while maintaining a horizontal orientation of the plate.

5. The device for culturing specimens of claim 1, wherein a lower portion of each plate holder is configured to support a plate thereon, and wherein the lower portion of each plate holder includes a transparent section extending through a thickness of the lower portion and configured for light transmission for imaging.

6. The device for culturing specimens of claim 1, wherein when the isolation chamber is in the second position, the conveyor is prevented from moving.

7. The device for culturing specimens of claim 1,
wherein a temperature within the housing is controlled such that the temperature within the housing is changeable based upon a schedule, and/or
wherein pressure within the housing is controlled to mimic typical intratubal or intrauterine pressure of a human female.

8. The device for culturing specimens of claim 1, wherein the device is further configured to agitate specimens disposed within the housing, and wherein agitation of the specimens is at a greater frequency or magnitude during daytime periods in a geographic location where the device is operated and at a lower frequency or magnitude during nighttime periods in the geographic location where the device is operated.

9. The device for culturing specimens of claim 1, wherein the device is further configured to have different conditions in different regions of the housing in order to reflect different physiological conditions that are experienced as an embryo moves from fallopian tubes into a uterine cavity or to reflect different uterine conditions that are experienced as an embryo incubates from day 1 to day 5 or 6.

10. The device for culturing specimens of claim 1,
wherein the device is further configured to monitor and record quality control (QC) information of specimens disposed within the housing and communicate the QC information to external equipment that is in communication with the device,
wherein the device is further configured to communicate developmental data regarding specimens disposed within the housing as monitored by the device with external laboratory management equipment, and/or
wherein the device is further configured to read bar code labeling of culture plates, RFID chips, or another device of wireless communication.

11. A device for culturing specimens, comprising:
a housing;
a conveyor disposed within the housing, the conveyor being translatable in vertical directions with respect to a plane the housing is disposed upon;
a plurality of plate holders disposed along a length of the conveyor, such that each plate holder of the plurality of plate holders can be moved to a first position and a second position along the length of the conveyor by a translation of the conveyor in the vertical directions; and
an isolation chamber movable between a third position and a fourth position, the isolation chamber including an opening and a door, wherein when the isolation chamber is in the third position, at least a portion of the isolation chamber is outside the housing, and when the isolation chamber is in the fourth position, at least the portion of the isolation chamber is inside the housing, and wherein the isolation chamber is configured such that when the isolation chamber is moved to the fourth position, a first surface of the isolation chamber sealingly engages a second surface of a first plate holder of the plurality of plate holders located in the first position.

12. The device for culturing specimens of claim 11, wherein the conveyor is translatable in a vertical plane with respect to the plane the housing is disposed upon or the conveyor has a helical or spiral configuration.

13. The device for culturing specimens of claim 11, further comprising an imaging system, the imaging system is configured and positioned such that when the first plate holder of the plurality of plate holders is located in the second position, an image of specimens placed on a plate that is supported by the first plate holder thereon can be captured by the imaging system.

14. The device for culturing specimens of claim 11, wherein when the isolation chamber is in the third position and the first plate holder is in the first position, the first plate holder is in registry with the opening of the isolation chamber.

15. The device for culturing specimens of claim 11,
   wherein each plate holder of the plurality of plate holders includes an upper portion configured to couple to the conveyor and a lower portion configured to support a plate thereon, and
   wherein each plate holder is configured such that when the upper portion is coupled to the conveyor, the lower portion extends horizontally.

16. The device for culturing specimens of claim 11, wherein each plate holder of the plurality of plate holders is configured for supporting a plate thereon such that the plate can be moved to different positions along the length of the conveyor by the translation of the conveyor in the vertical directions while maintaining a horizontal orientation of the plate.

17. The device for culturing specimens of claim 11, wherein the housing includes a front wall, wherein the front wall includes a section that is in registry with the opening of the isolation chamber when the isolation chamber is in the third position, and wherein the section is moveable such that a passageway can be formed on the front wall to allow the isolation chamber to be moved therethrough to the fourth position.

\* \* \* \* \*